(12) United States Patent
De Vreese et al.

(10) Patent No.: US 8,956,162 B2
(45) Date of Patent: Feb. 17, 2015

(54) STRIP FOR THE DELIVERY OF ORAL CARE COMPOSITIONS

(75) Inventors: Guy De Vreese, Sint-Martens-Latem (BE); Robin List, Hansbeke (BE)

(73) Assignee: Sylphar N.V., Duerle (BE)

( * ) Notice: Subject to any disclaimer, the term of this patent is extended or adjusted under 35 U.S.C. 154(b) by 0 days.

(21) Appl. No.: 13/528,174

(22) Filed: Jun. 20, 2012

(65) Prior Publication Data

US 2012/0322024 A1 Dec. 20, 2012

Related U.S. Application Data

(63) Continuation-in-part of application No. 11/918,168, filed as application No. PCT/EP2005/003779 on Apr. 11, 2005, now Pat. No. 8,753,612.

(51) Int. Cl.

| A61K 8/362 | (2006.01) |
|---|---|
| A61K 8/92 | (2006.01) |
| A61K 8/89 | (2006.01) |
| A61K 8/41 | (2006.01) |
| A61K 8/02 | (2006.01) |
| A61C 19/06 | (2006.01) |
| A61K 8/365 | (2006.01) |
| A61Q 11/00 | (2006.01) |
| A61K 31/192 | (2006.01) |
| A61K 31/405 | (2006.01) |
| A61K 31/407 | (2006.01) |
| A61K 31/5415 | (2006.01) |
| A61K 31/616 | (2006.01) |
| A61K 8/19 | (2006.01) |
| A61N 5/06 | (2006.01) |

(52) U.S. Cl.
CPC .............. *A61C 19/066* (2013.01); *A61K 8/362* (2013.01); *A61K 8/365* (2013.01); *A61Q 11/00* (2013.01); *A61K 31/192* (2013.01); *A61K 31/405* (2013.01); *A61K 31/407* (2013.01); *A61K 31/5415* (2013.01); *A61K 31/616* (2013.01); *A61C 19/063* (2013.01); *A61K 8/19* (2013.01); *A61N 2005/0606* (2013.01)
USPC ......................................... 433/217.1; 424/49

(58) Field of Classification Search
CPC ....................................................... A61C 19/06
USPC .......................................................... 424/49
See application file for complete search history.

(56) References Cited

U.S. PATENT DOCUMENTS

| 5,211,559 | A | 5/1993 | Hart et al. |
|---|---|---|---|
| 5,260,345 | A | 11/1993 | DesMarais et al. |
| 5,447,940 | A * | 9/1995 | Harvey et al. ................. 514/310 |
| 5,980,249 | A | 11/1999 | Fontenot |
| 6,551,579 | B2 | 4/2003 | Sagel et al. |
| 2002/0012685 | A1 | 1/2002 | Sagel et al. |
| 2002/0146666 | A1 | 10/2002 | Sagel et al. |
| 2004/0005277 | A1 | 1/2004 | Willison et al. |
| 2004/0062798 | A1 | 4/2004 | Lukenbach et al. |
| 2007/0178055 | A1 * | 8/2007 | Buch et al. ...................... 424/53 |

FOREIGN PATENT DOCUMENTS

| EP | 1405629 A2 | 4/2004 |
|---|---|---|
| EP | 1493452 A2 | 1/2005 |
| WO | 2004004799 A2 | 1/2004 |

\* cited by examiner

*Primary Examiner* — Walter Webb
(74) *Attorney, Agent, or Firm* — The Webb Law Firm

(57) ABSTRACT

Provided herein is a strip, shaped for the application to the labile surface of the front teeth and/or gums of a subject, which strip is provided with at least one oral care composition for delivery to a pre-determined area of the teeth and/or gums of the subject. Also provided herein are uses for delivery of compositions. Further provided are uses of the strip in combination with a dental device.

32 Claims, 2 Drawing Sheets

STRIP FOR THE DELIVERY OF ORAL CARE COMPOSITIONS

CROSS-REFERENCE TO RELATED APPLICATIONS

This application is a continuation-in-part application and claims the benefit of U.S. patent application Ser. No. 11/918,168, filed Nov. 14, 2007 and entitled "Foam Strip for the Delivery of Oral Care Compositions", which is a United States National Phase Application of International Patent Application No. PCT/EP2005/003779, filed Apr. 11, 2005, both of which are herein incorporated by reference.

FIELD OF THE INVENTION

The present invention relates to a strip comprising chemically inert, flexible, hydrophilic material, shaped for the application to the labile surface of the front teeth of a subject, which strip is provided with at least one oral care compositions for delivery to a pre-determined area of the teeth of the subject, said at least one oral care composition comprising a pharmaceutically acceptable multi-carboxylate salt. Further, the present invention relates to the use of said strip for the delivery of one or more oral care compositions for delivery to the pre-determined area of the teeth and/or gums of the subject. Furthermore, the present invention relates to a blister comprising said strip and to a kit comprising said strip.

It is an aim of the present invention to provide a new dental strip for the delivery of dental care agents which overcomes the problems of the prior art.

BACKGROUND TO THE INVENTION

Dental strips are known from the prior art, for example from U.S. Pat. No. 6,551,579 for delivery of oral care actives. In view of the prior art, there is a need for a dental strip which achieves good penetration between the teeth, without causing patient discomfort by applying undue pressure. Further, there is a need to overcome the problem of additional salivation owning to the presence of the strip in the mouth which causes harmful active agents such as bleaching agents to leech into the oral cavity. There is also a need for a dental strip for use in teeth whitening which indicates the progress of the whitening process. Furthermore, there is a need to provide a strip that renders the teeth less sensitive to the external medium such as when eating or drinking and that additionally provides the better adsorption of a component of an oral care composition. Yet another need is to provide a strip that allows a controlled and sustained release of an active component. Still another need is to provide a strip that allows the delivery of a component of an oral care composition on a pre-determined, or targeted, area.

SUMMARY OF THE INVENTION

These goals, amongst other goals, are achieved by the strip according to the present invention, as described below. One embodiment of the present invention is a strip comprising a chemically inert, flexible, hydrophilic material, shaped for the application to the labile surface of the front teeth of a subject, which strip is provided with at least one oral care compositions for delivery to a pre-determined area of the teeth of the subject, said at least one oral care composition comprising a pharmaceutically acceptable multi-carboxylate salt.

Another embodiment of the present invention is a strip as described above, wherein the pharmaceutically acceptable multi-carboxylate salt is an oxalate salt.

Another embodiment of the present invention is a strip as described above, wherein the the pharmaceutically acceptable multi-carboxylate salt is potassium oxalate.

Another embodiment of the present invention is a strip as described above, wherein the pharmaceutically acceptable multi-carboxylate salt is a di- or a tri-carboxylate salt.

Another embodiment of the present invention is a strip as described above, wherein the pharmaceutically acceptable multi-carboxylate salt is selected from the group adipate, aspartate, citrate, digluconate, fumarate, glucoheptanoate, maleate, oxalate, pamoate, succinate, tartrate.

Another embodiment of the present invention is a strip as described above, wherein the salt is an alkali metal salt.

Another embodiment of the present invention is a strip as described above, wherein the salt is a potassium salt.

Another embodiment of the present invention is a strip as described above, wherein the pharmaceutically acceptable multi-carboxylic salt is present in the oral care composition in an amount in the range 1% to 5% wt of the total weight of said at least one composition.

Another embodiment of the present invention is a strip as described above, wherein said material is a polyurethane, a polyester, a polyethylene, a cellulosic material, or a combination thereof.

Another embodiment of the present invention is a strip as described above, wherein said material is treated at least on one side with silicones, fluorocarbons, wax or a combination thereof.

Another embodiment of the present invention is a strip as described above, wherein said material is a polymer foam, a polymer film, a polymer gel or a combination thereof.

Another embodiment of the present invention is a strip as described above, wherein said material has a fluid capacity after compression of between 10 and 14 g water/g.

Another embodiment of the present invention is a strip as described above, wherein the material is a foam with a density between 70 and 180 kg/m$^3$.

Another embodiment of the present invention is a strip as described above, wherein said foam has a density between 90 and 150 kg/m3.

Another embodiment of the present invention is a strip as described above, wherein said material is a foam with a cell structure equal to or less than 220 micrometers.

Another embodiment of the present invention is a strip as described above, wherein said at least one oral care composition further comprises at least one teeth whitening agent.

Another embodiment of the present invention is a strip as described above, wherein said at least one teeth whitening agent is selected from the group consisting of metal ion free peroxides, organic peroxides, metal ion containing peroxides, metal chlorites, perborates, percarbonates, peroxyacids, monopersulfate, OXONE® (registered trademark of E.I. DuPont for monopersulfate oxidizing compound), ammonium persulfate, potassium persulfate, potassium monopersulfate, potassium peroxymonosulfate, potassium bisulfate, potassium sulfate and potassium peroxidisulfate, hydrogen peroxide, calcium peroxide, carbamide peroxide, urea peroxide, sodium percarbonate, sodium perborate, calcium hydroxide, calcium chlorite, barium chlorite, magnesium chlorite, lithium chlorite, potassium chlorate, hypochlorite, chlorine dioxide, magnesium carbonate and perhydrol urea and mixtures and derivatives thereof.

Another embodiment of the present invention is a strip as described above, wherein said at least one oral care composition further comprises one or more fluoride ions selected from the group consisting of sodium fluoride, potassium fluoride and ammonium fluoride.

Another embodiment of the present invention is a strip as described above, wherein said at least one oral care composition further comprises at least one antimicrobial agent.

Another embodiment of the present invention is a strip as described above, wherein said at least one antimicrobial agent is selected from the group consisting of 5-chloro-2-(2,4-dichlorophenoxy)-phenol, phthalic acid and its salts, substituted monoperthalic acid ant its salts and esters, magnesium monoperoxy phthalate, chlohexidine, alexidine, hexetidine, sanguinarine, bezalkonium chloride, salicylanilide, domiphen bromide, cetylpyridinium chloride (CPC), tertadecyl pridinium chloride (TPC), N-tetradecyl-4-ethylpyridinium chloride (TDEPC); octenidine; delmopinol, octapinol, nicin preparations, zinc/stannous ion agents, augmentin, amoxicilline, tetracycline, doxycylcine, monocycline, metronidazole, thymol, geraniol, carvacrol, citral, hinokitiol, eucalyptol, catechol, 4-allyl catechol, methyl salicylate, hydrogen peroxide and metal salts of chlorite.

Another embodiment of the present invention is a strip as described above, wherein said at least one oral care composition further comprises at least one or more anti-inflammatory agent.

Another embodiment of the present invention is a strip as described above, wherein said at least one anti-inflammatory agent is selected from the groups consisting of ketorolac, flurbiprofen, ibuprofen, naproxen, indometacin, aspririn, ketoprofen, piroxicam and meclofenamic acid.

Another embodiment of the present invention is a strip as described above, wherein said at least one oral care composition further comprises a nutrient selected from the group consisting of vitamins, oral nutritional supplements and enteral nutritional supplements.

Another embodiment of the present invention is a strip as described above, wherein said at least one oral care composition further comprises at least one antioxidant.

Another embodiment of the present invention is a strip as described above, wherein said at least one antioxidant is selected from the group consisting of Vitamin E, ascorbic acid, uric acid, carotenoids, Vitamin A, flavonoids and polyphenols, herbal antioxidants, melatonin, aminoindoles and lipoic acids.

Another embodiment of the present invention is a strip as described above, wherein said at least one oral care composition further comprises 5 to 8% peroxide, 0-5% potassium nitrate, a fluoride capable of releasing fluoride ions in a concentration of 0-5000 ppm, and 30-70% glycerine.

Another embodiment of the present invention is a strip as described above, wherein said at least one oral care composition further comprises at least one gelling agent.

Another embodiment of the present invention is a strip as described above, wherein said at least one gelling agent is selected form the group consisting of carboxypoly-methylene, caroxymethyl cellulose, caroxyproyl cellulose, poloxamers, carrageenan, Veegum, caroxyvinyl polymers and natural gums such as gum karaya, xanthan gum, Guar gum, gum Arabic, and gum tragacanth.

Another embodiment of the present invention is a strip as described above, wherein said at least one oral care composition is disposed on a reverse face.

Another aspect of the present invention is the use of the strip as described above, for the delivery of one or more oral care compositions for delivery to a pre-determined area of the teeth and/or gums of the subject.

Another embodiment of this other aspect of the present invention is the use as described above, combined with the use of a dental trough or brace.

Another embodiment of this other aspect of the present invention is the use as described above, wherein said dental trough or brace is capable of providing one or more or heat, light, mechanical stimulation and electrical stimulation directed towards the strip.

Another embodiment of this other aspect of the present invention is a use as described above for whitening teeth.

Yet another aspect of the present invention is a blister pack comprising one or more strips as described above.

Still another aspect of the present invention is a kit comprising one or more strips as described above and a dental trough or brace.

Another embodiment of the still other aspect of the present invention is a kit as described above, wherein said dental brace or trough is provided with heat, light, electrical stimulation and/or mechanical stimulation means.

The definitions, advantages and preferences defined herewith for the strip according to the present invention are applicable to all the aspects and all the embodiments of the present invention.

DETAILED DESCRIPTION OF THE INVENTION

The present invention relates to a strip (1), shaped for the application to the labile surface of the front teeth and/or gums of a subject, which strip is provided with at least one oral care composition for delivery to a pre-determined area of the teeth and/or gums of the subject. The labile surface refers to the surface which is normally proximal to the lips. The front teeth refers to at least those teeth visible when the jaw is closed, through parted lips.

Strip

Figure 1A:
FIG. 1. A view of an embodiment of a strip showing the front face (1a), top edge (1b) and reverse face (c).

Referring to the drawings particularly in FIGS. 1a (front view), 1b (plan view) and 1c (reverse view), the strip 1 is approximately oblong shaped and is initially substantially flat. Applied or coated onto at least part of the strip 1 are one or more oral care compositions. It may be uniformly and continuously coated onto the strip. The composition may, alternatively, be a laminate or separated layers of components, an amorphous mixture of components, separate stripes or spots or other patterns of different components or a combination of these structures, including a two stripes of continuous of oral care composition along a longitudinal axis of the reverse face of the strip 2.

According to one embodiment of the invention the dental care composition is provided evenly across the reverse face of the strip 1. It is an aspect of the present invention that the composition is provided as a concentration gradient on the strip, which gradient may run in the direction of the width or the length of the strip, or both. For example, the strip may be disposed with a higher concentration of whitening composition in the centre and biting edge of the strip, and a lower concentration towards the gingival edge of the strip. Alternatively or in addition, the strip may be disposed with a higher concentration of whitening composition in the region of the front incisors, and a lower concentration towards the sides. In another embodiment, the dental care composition's concentration may vary across several strips in the same package.

According to another embodiment of the invention, where a strip contacts both the gums and the teeth, the strip is provided with a different composition for each of the gum and the teeth. For example, the portion of the strip in contact with the teeth may be provided with teeth whitening agent, while the portion in contact with the gums may be provided with vitamins or any other healthy-gum promoting substance or with a desensitizing/anti-oxidant chemical. Said configuration may further be provided in a gradient.

The strip 1 is made of a flexible, hydrophilic polyurethane material which is chemically inert. The term "flexible" can also be designated as "open cell". The material is preferably of medical grade. The material preferably has no memory effect i.e. it returns to its original shape after manipulation. The strip preferably comprises a continuous strip of material. In the context of the present invention, said material is a polymer foam, a polymer film, a polymer gel or a combination thereof.

The material of the strip can be any polymeric materials. By polymeric material, it is to be understood in the context of the present invention, any homopolymeric or copolymeric materials. The polymeric material can be any homopolymers of a polyurethane, a polyester, a polyethylene, for example. The polymeric material can also be a copolymer of a polyurethane, a polyester, a polyethylene. In the context of the present invention, the homopolymer or copolymer can be any polyurethane, polyester, or polyethylene. Specifically, it can be any substituted or unsubstituted polymer of polyurethane, polyester or polyethylene providing the properties of being chemically inert, flexible and hydrophilic. Advantageously, a substituted polymer as described above comprises one or more substitutions. The substitution can be an alkyl substitution or a functional group chosen from the group: hydroxy (—OH); ether (—O—R) wherein R represents —H, or an alkyl; aldehydes (—CHO), carboxy (—COO—R), wherein R represents —H, or an alkyl. The material of the strip according to the present invention can also be a mixture of polymers, in other words it can be made of more than one polymer, such as polymers that did not react with each other but form a layered, or laminated structure of at least two polymers.

Another embodiment of the present invention is a strip as described above, wherein said material is a polyurethane, a polyester, a polyethylene, a cellulosic material, or a combination thereof.

According to the present invention, the strip can be treated at least on one side with silicones, fluorocarbons, wax or a combination thereof. In the context of the present invention, silicones are inert, synthetic compounds that are temperature-resistant and rubber-like. Silicones are polymers that include the silicon element (Si) together with carbon, hydrogen, oxygen, and sometimes other chemical elements, such as nitrogen, or sulfur. Some common forms include silicone oil, silicone grease, silicone rubber, and silicone resin. In the context of the present invention, fluorocarbons are also designated as perfluorocarbons or PFCs. Flurocarbons are organofluorine compounds that contain carbon and fluorine bonded together in strong carbon-fluorine bonds. In the context of the present invention, the fluorocarbons containing only carbon and fluorine, but may contains some fluorine, carbon and other elements, such as hydrogen (these last compounds are also designated as fluoroalkanes). Examples of fluorocarbons can be chlorofluorocarbons as well as perfluorinated compounds. In the context of the present invention, a wax is to be understood as a class of chemical compounds that are plastic (malleable) near ambient temperatures. Characteristically, they melt above 45° C. (113° F.) to give a low viscosity liquid. Waxes are insoluble in water but soluble in organic, nonpolar solvents. All waxes are organic compounds, both synthetic and naturally occurring, that characteristically consist of long alkyl chains. Natural waxes are typically esters of fatty acids and long chain alcohols. Synthetic waxes are long-chain hydrocarbons lacking functional groups.

The hydrophilic polyurethane materials are made based on the technology of hydrophilic polyurethane prepolymers. The prepolymer which is used in the method of the invention is preferably an isocyanate-capped polyether, such as an polyethyleneoxide or an ethyleneoxy/propyleneoxy copolymer. A suitable prepolymer is described in GB-A-1 429 711 and in WO96/16099 U.S. Pat. No. 6,271,277 or U.S. Pat. No. 4,008, 189. Suitable prepolymers are commercially available under the Trade Mark HYPOL (Dow Chemical) or as Optipol (LMI). The presence of unreacted isocyanate functionalities in the prepolymer leads to formation of the foam structure when mixed with appropriate amounts of ater. Furthermore, it is an important aspect of the foam currently in use that there are no metal catalysts (e.g. Sn (II)) used for the production of neither the prepolymer nor the foam itself.

Polyester materials are a category of polymers which contain the ester functional group (—COO—) in their main chain. A specific material most commonly refers to polyethylene terephthalate (PET). Polyesters include naturally occurring chemicals, as well as synthetics through step-growth polymerization such as polycarbonate and polybutyrate. Natural polyesters and a few synthetic ones are biodegradable, but most synthetic polyesters are not. Depending on the chemical structure, polyester can be a thermoplastic or thermoset; most polyesters are thermoplastics. Examples of polyester polymers (homo- or copolymers) are polyglycolic acid (PGA), polylactic acid (PLA), polycaprolactone (PCL), polyethylene adipate (PEA), polyhydroxyalkanoate (PHA), polyethylene terephthalate (PET), polybutylene terephthalate (PBT), polytrimethylene terephthalate (PTT), polyethylene naphthalate (PEN). Polyethylene is abbreviated PE and has the IUPAC name polyethene or poly(methylene). The chemical formula of PE is $(C_2H_4)_nH_2$. In the context of the present invention, they can be any type of polyethylenes, subsititited or not and the material can also be a similar organic compound that differ in terms of the value of n, in the chemical formula of PE indicated above.

Cellulosic materials are materials that comprise cellulose, which is an organic compound with the formula $(C_6H_{10}O_5)_n$, in other words a polysaccharide consisting of a linear chain of several hundred to over ten thousand $\beta(1 \rightarrow 4)$ linked D-glucose units.

The material of the strip is advantageously a polymer foam, a polymer film, a polymer gel, or a combination thereof.

A foam may be prepared using any method which provides a suitable foam according to the present invention. According one embodiment of the invention a flexible hydrophilic foam may be prepared according to the process described in U.S. Pat. No. 4,008,189 using reaction mixture comprised of an organic polyisocyanate, a foaming agent, a reaction catalyst, and three polyether polyols, namely.

a. a first polyol having a molecular weight of about 3000-5000 which is the product of sequentially oxyalkylating an aliphatic triol first with ethylene oxide and then with propylene oxide using a molar ratio, ethylene oxide:propylene oxide, from about 0.3:1 to about 1.6:1, said first polyol being used in a weight proportion from about 10 to about 50 percent of the combined weights of said three polyols, b. a second polyol having a molecular weight of about 2000-5000 which is the product of sequentially oxyalkylating an aliphatic diol first with ethylene oxide and then with propylene oxide using a molar ratio, ethylene oxide:propylene oxide, from about 0.3:1 to about 1.4:1, said second polyol being used in a weight proportion of about 20-50 percent of the combined weights of said three polyols, and c. a third polyol having a molecular weight of about 2400-5000 which is the product of oxyalkylating an aliphatic triol with a random mixture of ethylene oxide and propylene oxide, the content of ethylene oxide in the mixture being about 5-25% by weight, said third polyol being used in a proportion of about 10-50 percent of the combined weights of said three polyols.

According to one aspect of the invention, the density of the foam is between 70 to 180 kg/m$^3$, 80 to 170 kg/m$^3$, 80 to 150 kg/m$^3$, or 90 to 150 kg/m$^3$. Preferably it is 70 to 150 kg/m$^3$.

A density of 120 (+/−30) kg/m3 is a suitable density. Density may be measured according to the test EN/ISO 845: 1988 Mod2.

The foam of the present invention has preferably an open-celled, very fine cell structure. According to another aspect of the invention, the cell structure (Visiocell) of the foam has an average diameter is equal to or less than 50, 100, 150, 200, 220, 250, 300, 350, 400, 450, 500 micrometers or a value between in the range between any two of the aforementioned diameters. Preferably, the diameter is less than 220 micrometers, and more preferably between 100 to 150 micrometers.

According to another aspect of the invention, the wet out of the foam is equal to or lower than 500, 450, 400, 350, 300, 250, 300, 150, 100, 50, 25, 10, 6, 5, 4, 3, 2, or 1 s or is a value in the range between any two of the aforementioned values. Preferably it is between 1 and 5 s, or less than 5 s. The wet out may be measured according to the standard test or according to the method described in EP 1 493 452.

According to another aspect of the invention, fluid capacity of the foam after draining is equal to or higher than 2, 3, 4, 5, 6, 7, 8, 10, 11, 12, 13, 14, 15, 16, 17, 18, 20, 21, 22, 23, 24, 25 g water/g foam or is a value in the range between any two of the aforementioned values. It is preferably between 18 and 20 water/g foam. The fluid capacity of the foam after draining may be measured according to the standard test described in EN 13726-1 or according to the method described in EP 1 493 452.

According to another aspect of the invention, fluid capacity of the foam after saturation is equal to or higher than 1, 1.5, 2, 2.5, 3, 4, 5, 6, 7, 8, 9, 10, 11, 12, 13, 14, 15, 16, 17, 18, 29, 20 g water/g foam or is a value in the range between any two of the aforementioned values. It is preferably higher than 1.5 water/g foam. The fluid capacity of the foam after compression may be measured according to the method described in EP 1 493 452.

According to another aspect of the invention, fluid capacity of the foam after compression is equal to or higher than 4, 5, 6, 7, 8, 9, 10, 11, 12, 13, 14, 15, 16, 17, 18, 29, 20 g water/g foam or is a value in the range between any two of the aforementioned values, and is preferably between 10 and 14 water/g foam. The fluid capacity of the foam after compression may be measured according to a standard test described in EN 13726-1 above.

Preferably the strip is VIVO foam MCF.03 or an equivalent thereof (Copura/Reticel). For clarity only, the properties of MCF.03 are listed in Table 1. However, it is by no means the intention to limit the present invention to foam having the particular characteristics of MCF.03. It is a embodiment of the invention that a foam has the characteristics as indicated in Table 1, within a tolerance of +−20%, +−18%, +−16%, +−14%, +−12%, +−10%, and preferably +−20%.

In regard of the Table 1, MVTR stands for "Moisture Vapor Transmission Rate" which is a measure of the passage of gaseous water through a barrier. It is also know as "WVTR", or "Water Vapor Transmission Rate". Moisture resistance is commonly measured in a special chamber, divided vertically by the substrate/barrier material. A dry atmosphere is present in one chamber, and a moist atmosphere in the other. A 24-hour test is made to see how much moisture passes through the substrate/barrier from the "wet" chamber to the "dry" chamber. Standard test procedures (TAPPI T-464, ASTM E96) can specify any one of five combinations of temperature and humidity in the "wet" chamber. ER/RR is a measure of the tensile strength (in kPa) and the elongation at break. It is described in standard ISO 1798:1997. CDH indicates a method for the calculation of the compression stress value of cellular flexible polymers with a density of less than 250 kg/ml. The compression stress/strain characteristic is a measure of the load-bearing properties of the material. It is described in standard ISO 3386-1:1986.

A polymer film in the context of the present invention can be a thin film or a film comprising a multilayer of polymer. It can be made by any known technique for polymer film fabrication. Examples of such techniques are for depositing a thin film of material onto a substrate or onto previously deposited layers, such as spin coating, chemical deposition or dipping. By film is to be understood layer of material ranging from fractions of micrometers to a few hundreds of micrometers in thickness.

A polymer gel in the context of the present invention is a solid material that can have properties different properties of hardness. In the context of the present invention, the polymer gel is defined as a substantially dilute cross-linked system, which exhibits no flow when in the steady-state. It is the crosslinks within the fluid that give a gel its structure (hardness) and contribute to stickiness.

The material of the strip according to the present invention can be a combination of a polymer foam, and/or a polymer film, and/or a polymer gel. It can be layered, or laminated, structure comprising at least two layers, such as two layers, three layers, four layers, five layers, six layers. The layers can be all different, or identical. In the case a polymer film is coated on a polymer foam and/or on a polymer gel, the film may be a thin film and have one nanometer or a few nanometers thickness. By a few nanometers thickness it is to be understood any value from 2 nm to 100 nanometers. The structure of the strip can comprise a substantially planar adhesive coated side and a second side. Advantageously, the composition of the two sides of the strip is different.

The material of the strip is preferably a conductor of heat (i.e. not considered an insulator).

The inventors have found that the use of a hydrophilic material conveys several advantages to the delivery of an agent. For example, the material is soft and flexible to contact the contours of the oral surface so evenly distributing agents across the surface. The soft texture of the material provides little or no abrasion to the oral surface, therefore, the strip can be maintained for prolonged periods without irritation. The flexibility enables the strip 1 to cover the contours of the oral surface with minimal external force. The flexibility of the material is such that the inherent forces are not sufficient to return the material to the initial flat state once attached to the teeth or gums. Thus the material is compatible for use with adhesives, trough or brace, which bend the material for application to the teeth or gums.

Figure 2:
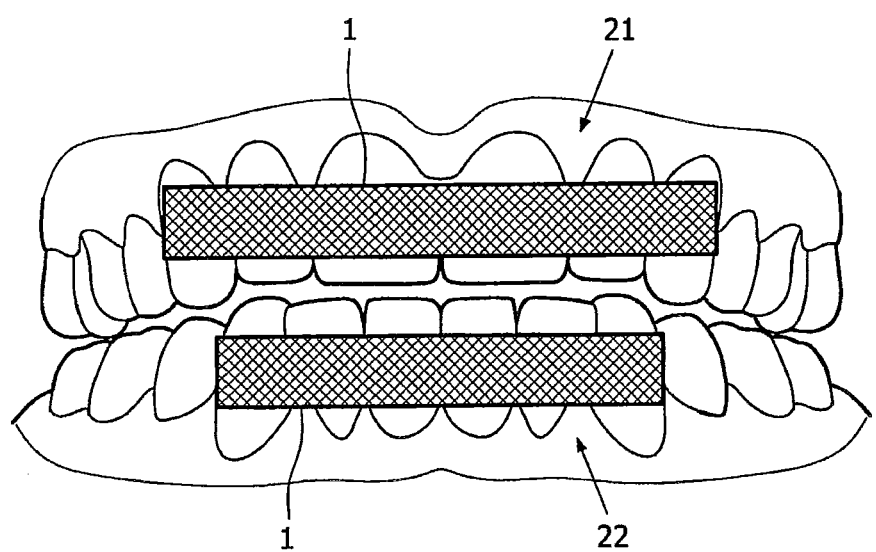
FIG. 2. A view of two strips according to the present invention applied to the labile surfaces of the upper and lower teeth.

Referring to FIG. 2, the strip 1 can be applied to the teeth of the upper dental arch 21 and/or lower dental arch 22. The flexibility enables the strip 1 to cover the contours of the oral surface with a requirement for a minimal of external force. Thus, the strip 1 can be maintained in position using weak adhesives, and still provide sufficient close association between the enamel and strip 1 for effective delivery of oral care compositions.

The strip 1 can also be used in combination with dental device such as a trough or brace. Said devices are shaped to fit the teeth and comprise a means for supporting a strip 1 during treatment. It is a further aspect that the dental device provides additional functionality such as heat, light, mechanical or electrical stimulation to enhance the effect of the oral care composition. When used in combination with a trough or brace, the pressure exerted by the device towards the enamel of the teeth is absorbed by the strip 1. The material cushions the user from the brace or trough and distributes evenly pressure therefrom.

The hydrophilic property of the material prevents the oral care composition from leeching beyond the intended delivery area i.e. from beyond the surface of the material which contacts the oral surface. Where the strip 1 is used to deliver caustic substances such as bleaching agents, the harmful effects due to application to areas other than the enamel are minimized.

During use, the material may swell up which leads to an enhanced fitting and penetration of oral apertures.

Often a subject generates additional saliva in response to the presence of oral intrusion. Swallowing the saliva during teeth whitening, for example, is often advised against, as a precaution, in case the saliva is contaminated with bleaching agent. If the subject could swallow the peroxide contaminated saliva, a local irritation or allergy may arise. Thus a subject experiences discomfort during treatment by refraining from swallowing. The absorptive and retentive capacity of the material, such as a foam or a gel, for example, absorbs excess saliva and prevents leeching of otherwise harmful substances back into the oral cavity. Therefore, the strip alleviates the buildup of excessive saliva, allowing the subject to wear the strip for prolonged periods where necessary.

The strip 1 facilitates the steady and measured release of oral care agents by providing a low pressure contact area across which agents can move. In other words, one of the advantages of the present invention is that the strip provides controlled and sustained release of an active component of an oral care composition. Unlike other means for delivery, no abrasive or intrusive actions are necessary to deliver the agent. The rate of release can be controlled by the viscosity of the oral care composition.

The at least one oral care composition provided with the strip according to the present invention is delivered to a pre-determined area of the teeth. The strip provided with the at least one oral care composition according to the present invention allows the delivery of the at least one oral care composition on said pre-determined area. In the context of the present invention, the term "pre-determined area" means an area where the strip is applied and an area comprising said at least one oral care composition. The pre-determined area can also be designated as "target area" or "specific area". The pre-determined area is the area of the teeth to be treated via the application of the strip according to the present invention provided with at least one oral care composition according to the present invention. The pre-determined area can be a part of a tooth, one tooth, more than one tooth, several teeth, such as two, three, four, five, six, seven, eight, nine, ten, eleven, twelve, thirteen, fourteen, fifteen, sixteen teeth. The pre-determined area can be any part of the enamel of the tooth, such as an area close to the gum. The labile surface wherein the strip is applied and the pre-determined area wherein the delivery of the at least one oral care composition is carried out may be the same or may be different.

The hydrophilic property of the material also allows waste products to be absorbed. For example during the whitening of teeth using a bleaching agent, the substances responsible for staining (e.g. tartar and other types of buildup) become more hydrophilic. The solubilized stains are absorbed by the hydrophilic foam, so exposing a new surface of unsolubilized staining for the bleaching agent to react with.

Furthermore, the use of a light colored material (e.g. cream or white) enables the user to visualize the progress of the whitening process. As the solubilized staining is absorbed into the material, the surface of the material discolors according to the degree of staining removed.

Thus the material provides an indication of when the treatment is complete, when discoloration stops.

According to one embodiment of the invention the strip 1 is less than 0.5 mm, 1 mm, 1.5 mm, 2 mm, 2.5 mm, 3 mm, 3.5 mm, 4 mm, 2.5 mm, 5 mm, 5.5 mm, 6 mm, 6.5 mm, 7 mm, 7.5 mm, 8 mm, 8.5 mm, 9 mm, 9.5, 10 mm, 10.5 mm or 11 mm thick, or of a thickness between any two of the aforementioned values. Preferably, one type of strip is between 0.5 and 4 mm thick and another type of strip is between 4 mm and 8 mm thick. The thickness of the strip depends of the nature (material and/or sort of material, such as foam, film, gel or any combination thereof).

Figure 1B:
Figure 1C:
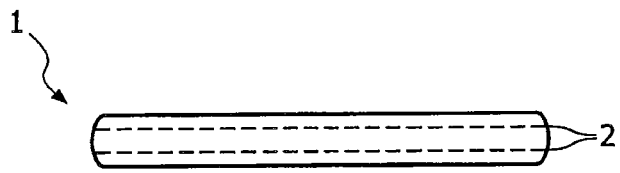

The shape of the strip 1 is any shape and size that covers the desired teeth and/or gums of the subject. The strip 1 may have rounded edges, square edges, angled edges, or the edges may be shaped suitably for insertion into the mouth and close association with the teeth. The strip 1 may be lozenge shaped, trapezium shaped, isosceles trapezium shaped or adopt a shape according to FIG. 1. According to one embodiment, the strip may be reduced in width at the edges so that the strip does not contact the gums or gingival where, for example, the strip is provided with peroxide. According to one embodiment of the invention, the length of the strip 1 may be less than 1, 2, 3, 4, 5, 6, 7, 8, 9, 10, 11, 12, 13, 14, 15 cm, or a value between any two of said distances. Preferably the strip is between 5 and 8 cm long. According to one embodiment of the invention, the width of the strip 1 may be less than 0.2, 0.3, 0.4, 0.5, 0.6, 0.7, 0.8, 0.9, 1, 1.5, 2, 2.5, or 3 cm, or a value between any two of said distances. Preferably the strip 1 is between 0.5 and 0.9 cm wide.

The strip 1 may be disposed with shallow pockets which provide reservoirs of oral care composition. Preferably, a strip 1 comprises an array of shallow pockets. The shallow pockets may be less than 0.5, 0.4; 0.3, 0.2, 0.1 mm deep or a value between any two of said depths. The shallow pockets may be less than 8, 7, 6, 5, 4, 3, 2 or 1 mm across, or a value between any two of said distances. The shallow pockets are preferably 0.5 mm deep and 4 mm across.

The oral care composition may be present within cavities in the material as described above, within the body of the foam, on one or both surfaces of the strip 1, or a combination of these. Preferably, the oral care composition is disposed on one surface of the strip 1.

It is an aspect of the invention that the front face of the strip 1 (FIG. 1a), not intended for contact with the teeth, is printed. By printed it is means said surface is colored, provided with a pattern, graphic or photograph, provided with written information or a combination of these. Where the surface is printed with written information, said information may be, for example, instructions for use, an indication of the oral care composition etc.

Oral Care Composition

The oral care composition according to the present invention comprises a pharmaceutically acceptable multi-carboxylic salt. Accordingly, the composition comprises an acid salt, more particularly a carboxylic acid salt, most particularly a multi-carboxylate salt. In the context of the present invention, a multi-carboxylate salt is a salt of a carboxylic acid, comprising more than one carboxylate (—COO—) moiety, such as two carboxylate moieties, three carboxylate moieties, four carboxylate moieties, five carboxylate moieties, six carboxylate moieties. A multi-carboxylate salt comprising two carboxylate moieties is designated as a di-carboxylate salt, a salt comprising three carboxylate moieties is designated as a tri-carboxylate salt, a salt comprising four carboxylate moieties is designated as a tetra-carboxylate salt, a salt comprising five carboxylate moieties is designated as a penta-carboxylate salt, a salt comprising six carboxylate moieties is designated as an hexa-carboxylate salt. Preferred are di- or tri-carboxylate salts. The counter ions of these salts are preferably chosen from alkaline metal cations, or the ammonium ion.

Specifically, advantageous properties have been obtained wherein the pharmaceutically acceptable salts is a salt of a multi-carboxylic acid selected from the group adipate, aspartate, citrate, digluconate, fumarate, maleate, oxalate, pamoate, succinate, tartrate.

Adipate ($^-OOC—(CH_2)_4—COO^-$) is the deprotonated anion of adipic acid. Adipate presents the advantage of regulating the acidity of the strip according to the present invention, specifically by modulating the pH, resulting in zero-order release of other hydrophilic components of the strip.

Aspartate has the chemical formula $^-OOCCH(NH_2)CH_2COO^-$ and presents the advantage of providing a certain sweetness to a strip according to the present invention.

Citrate is the conjugate base of citric acid and has the chemical formula ($C_3H_5O(COO)_3^{3-}$). The advantages of citrate salts are an anticoagulant effects, or can be used as nutritional supplements when combined with a specific counter ion, such as iron, for example.

Digluconates have anti-bacterial properties.

Fumarate ($^-O_2CCH=CHCO_2^-$, configuration trans) is a compound with the molecular formula $C_4H_2O_4^{2-}$ and is the salt of fumaric acid. Fumarate can be used as an acidity regulator. Sodium fumarate and fumaric acid are sometimes used as terminal electron acceptors.

Maleate is the ionized form of maleic acid. The maleate ion is useful in biochemistry as an inhibitor of transaminase reactions. Maleate has the formula $^-O_2CCH=CHCO_2^-$ (configuration cis).

Oxalate is also designated with the IUPAC name ethanedioate, Oxalate is the dianion with formula $C_2O_4^{2-}$ also written $(COO)_2^-$. Oxalate also forms coordination compounds. When present in the strip according to the present invention, an oxalate salt provides a whitening effect.

Pamoate also designated as 4-[(3-Carboxy-2-hydroxynaphthalen-1-yl)methyl]-3-hydroxynaphthalene-2-carboxylic acid.

Succinate has the formula $^-O_2CCH_2CH_2CO_2^-$ and can be used to control acidity.

Tartrate is a salt of the tartaric acid, a dicarboxylic acid and has the formula $^-OOC—CH(OH)—CH(OH)—COO^-$. Tartrate can be used as an antioxidant or an emulsifier.

The salts described above present the advantage that when the strip according to the present invention is provided with at least one oral care composition for delivery to the teeth and/or gums of the subject, in particular for delivery to a pre-determined area of the teeth and/or gums of the subject, which composition comprises a pharmaceutically acceptable salt, in particular chosen from a di-carboxylic or tri-carboxylic salt as described above, a particular and surprising effect is observed. Specifically, the pharmaceutically acceptable salt herewith is used as a component of the strip according to the present invention, the teeth present less sensitivity to external conditions, such as the ingestion of warm or cold food, or warm or cold drinks. Further, another advantage is that the strip provides controlled and sustained release of an active component of an oral care composition.

Advantageously, the di-carboxylic or tri-carboxylic salt is selected from the group adipate, aspartate, citrate, digluconate, fumarate, maleate, oxalate, pamoate, succinate, tartrate.

More advantageously, the salt comprises a cation of an alkali metal, such as sodium or potassium. More particularly, the salt is sodium oxalate, or potassium oxalate. A preference is give for potassium oxalate.

In the context of the present invention, the pharmaceutically acceptable multi-carboxylic salt is present in the oral care composition in an amount in the range 1% to 5% wt. of the total weight of said at least one oral care composition. The pharmaceutically acceptable multi-carboxylic salt is present in the oral care composition in an amount of at least 1% wt., preferably at least 1.5% wt. of the total weight of said at least one oral care composition. The pharmaceutically acceptable multi-carboxylic salt is present in the oral care composition in an amount of at most 5% wt, preferably at most 4.5% wt, more preferably at most 4% wt. of the total weight of said at least one oral care composition. The amount of multi-carboxylic salt have any value between the range described above, such as 1% wt., 1.5% wt., 2% wt., 2.5% wt., 3% wt., 3.5% wt, 4% wt., 4.5% wt, 5% wt. of the total weight of said at least one oral care composition. The amount of multi-carboxylic salt have any value between the range described above, such as in the range 1% to 4.5% wt. of the total weight of said at least one oral care composition, 1.5 to 4% wt. of the total weight of said at least one oral care composition.

In the context of the present invention, the oral care composition can comprise one or more further oral care agents. Said agents include any substance that is generally considered as safe for use in the oral cavity that can provide changes to the overall health of the oral cavity, and specifically the condition of the oral surfaces the oral care substance contacts. Oral care compositions of the present invention may include many of the agents previously disclosed in the art. The following is a non all-inclusive list of oral care agents that may be used in the present invention either separately or as a combination of two or more.

Preferably, the viscosity of a dental care composition is less than 2500, 5 000, 10 000, 15 000 centipoise at a shear rate of 50 per second. The viscosity may be adjusted by the addition of glycerine or other humectants such as, sorbitol, polyethylene glycol, propylene glycol, and other edible polyhydric alcohols. Preferably, the dental care composition has little or no binder. It is an aspect of the invention that the dental care composition comprises an aromatic agent such as spearmint or peppermint. It is another aspect of the current invention that the preferred formulation contains a detergent or soap. (e.g. polysorbate 80).

Teeth Whitening Agents

A composition of the present invention may comprise one or more teeth whitening agents. Examples of teeth whitening agents are known in the art and include but are not limited to oxygen radical generating agent such as metal ion free peroxides, organic peroxides, metal ion containing peroxides, metal chlorites, perborates, percarbonates, peroxyacids and combinations thereof. Specific, non-limiting examples of teeth whitening suitable for use with the invention are redox agents such as monopersulfate, Oxone, ammonium persulfate, potassium persulfate, potassium monopersulfate, potassium peroxymonosulfate, potassium bisulfate, potassium sulfate, and potassium peroxidisulfate. Additional specific, non-limiting examples of teeth whitening suitable for use with the device of the invention are the peroxide class of bleaching agents such as hydrogen peroxide, calcium peroxide, carbamide peroxide, (it is the same as carbamide peroxide), sodium percarbonate, sodium perborate, calcium hydroxide, calcium chlorite, barium chlorite, magnesium chlorite, lithium chlorite, potassium chlorate, hypochlorite, chlorine dioxide, magnesium carbonate and it is the same as carbamide peroxide and mixtures and derivatives thereof.

In a preferred embodiment of the invention, a teeth whitening oral care composition comprises peroxide, potassium nitrate, fluoride and an edible polyhydric alcohol.

Where the peroxide is hydrogen peroxide, the concentration may equal to or less than 0.01, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35% peroxide, or a value within the range of any of the two of the aforementioned concentrations. It may be between 0.01 and 35%, more preferably 5 and 25%, more preferably 5 and 10%, most preferably 5 and 8%. Alternatively, the concentration of H2O2 in combination with one of the compounds mentioned above, is such that such that H2O2 is released the amount between 0.01 and 35%, more preferably 5 and 25%, more preferably 5 and 10%, most preferably 5 and 8%.

The concentration of potassium nitrate may be between 0 and 15%, more preferably 0 and 5%, and most preferably 0.01 and 2%.

The fluoride may be any chemical capable of releasing fluoride ions in a concentration of 0 to 25000 ppm, more preferably 0 to 5000, most preferably 1000 to 1500 ppm measured as F<−> ion.

The concentration of edible polyhydric alcohol (e.g. glycerine) may be between 1 and 80%, more preferably 30 and 70%, more preferably 40 and 60%.

In another preferred embodiment, a teeth whitening composition comprises the components according to Table 2. It is a embodiment of the invention that a teeth whitening composition comprises the components according to Table 2, within a variation of +−20%, +−18%, +−16%, +−14%, +−12%, +−10%, and preferably +−20% of the quantity of components except water, the total m/m % being made up to 100 with water.

The skilled person can adjust the amount of peroxide present in the foam by adjusting the amount of teeth whitening composition sprayed onto the foam. Table 3 below indicates non-limitative examples of foam disposed with different amounts of the composition in Table 2 above, and the concentration of peroxide in the foam resulting therefrom. Thus, the skilled person can vary the amount of H2O2 in the foam by varying the amount of composition added.

The teeth whitening composition of Table 2 may be realized by using one or more of sorbitol, propylene glycol, polyethylenglycol, syropus simplex, glucose syrup, or any other edible polyhydric alcohol in addition to or in place of glycerine. The amount of said substance(s) is preferably within the range mentioned above for glycerine.

Any peroxide releasing compound (e.g. carbamide peroxide) can used in place of or in addition to hydrogen peroxide. The total amount of said peroxide releasing compound is preferably such that the amount of hydrogen peroxide released is within the range mentioned above for hydrogen peroxide (e.g. ca. 25 m/m for carbamide peroxide).

The following substances are preferred alternatives for EDTA in the composition of Table 2: phosphonic acids and their salts in concentrations between 0.001 and 5%, with optimum concentration between 0.05 and 0.5%; citric acid and citrate salts, with a comparable concentration range; polyphosphates and phosphates with different counter ions.

The following substances are preferred alternatives for BHT in the composition of Table 2: any anti-oxidant known in the art such as: Vitamin E, ascorbic acid, Uric acid, carotenoids, Vitamin A, flavonoids and polyphenols, herbal antioxidants, melatonin, aminoindoles, lipoic acids in concentrations as known to a person skilled in the art, and within legislative limits.

The following substances are preferred alternatives for sodium hydroxide in the composition of Table 2: potassium hydroxide, ammonium hydroxide, mono-, di- and/or tribasic sodium phosphate or potassium phosphate or any combination of these. Eventually, any other base may be used.

In addition, a teeth whitening composition of the present invention may further comprise one or more aroma compound, any natural, synthetic or semi-natural compound may be used. The aromas used are preferably water-soluble or are made water-soluble by using well-known techniques.

Preferably the teeth whitening composition is polar so that resulting whitened teeth are in the hydrated state, unlike the use of apolar compositions which indicate a false degree of whitening after treatment. The teeth whitening composition may not necessarily be adhesive per se, but can achieve adhesion to the teeth because of the polarity of the composition.

Preferably the pH is adjusted using sodium hydroxide rather than trietholamine. The pH of a teeth whitening composition is in the range of 6.2 to 7.7, and is preferably 6.5. Preferably, the teeth whitening composition has little or no binder.

Phosphates

A composition of the present invention may comprise one or more anti-tartar agents. Such agents known for use in dental care products include phosphates. Phosphates include pyrophosphates, polyphosphates, polyphosphonates and mixtures thereof. Pyrophosphates are among the best known for use in dental care products. Pyrophosphate ions are delivered to the teeth derive from pyrophosphate salts. The pyrophosphate salts useful in the present compositions include the dialkali metal pyrophosphate salts, tetra-alkali metal pyrophosphate salts, and mixtures thereof. Disodium dihydrogen pyrophosphate (Na2H2P2O7), tetrasodium pyrophosphate (Na4P2O7), and tetrapotassium pyrophosphate (K4P2O7) in their unhydrated as well as hydrated forms are the preferred species. While any of the above mentioned pyrophosphate salts may be used, tetrasodium pyrophosphate salt is preferred.

The pyrophosphate salts are described in more detail in Kirk & Othmer, Encyclopedia of Clinical Technology Third Edition, Volume 17, Wiley-Interscience Publishers (1982), incorporated herein by reference in its entirety, including all references incorporated into Kirk & Othmer. Additional anti-calculus agents include pyrophosphates or polyphosphates disclosed in U.S. Pat. No. 4,590,066 issued to Parran & Sakkab on May 20, 1986; polyacrylates and other polycarboxylates such as those disclosed in U.S. Pat. No. 3,429,963 issued to Shedlovsky on Feb. 25, 1969 and U.S. Pat. No. 4,304,766 issued to Chang on Dec. 8, 1981; and U.S. Pat. No. 4,661,341 issued to Benedict & Sunberg on Apr. 28, 1987; polyepoxysuccinates such as those disclosed in U.S. Pat. No.

4,846,650 issued to Benedict, Bush & Sunberg on Jul. 11, 1989; ethylenediaminetetraacetic acid as disclosed in British Patent No. 490,384 dated Feb. 15, 1937; nitrilotriacetic acid and related compounds as disclosed in U.S. Pat. No. 3,678,154 issued to Widder & Briner on Jul. 18, 1972; polyphosphonates as disclosed in U.S. Pat. No. 3,737,533 issued to Francis on Jun. 5, 1973, U.S. Pat. No. 3,988,443 issued to Ploger, Schmidt-Dunker & Gloxhuber on Oct. 26, 1976 and U.S. Pat. No. 4,877,603 issued to Degenhardt & Kozikowski on Oct. 31, 1989; all of these patents are incorporated herein by reference. Anticalculus phosphates include potassium and sodium pyrophosphates; sodium tripolyphosphate; diphosphonates, such as ethane-1-hydroxy-1,1-diphosphonate, 1-azacycloheptane-1,1-diphosphonate, and linear alkyl diphosphonates; linear carboxylic acids; and sodium zinc citrate.

Agents to may be used in place of or in combination with the pyrophosphate salt include such known materials as synthetic anionic polymers including polyacrylates and copolymers of maleic anhydride or acid and methyl vinyl ether (e.g., Gantrez), as described, for example, in U.S. Pat. No. 4,627,977, to Gaffar et al., the disclosure of which is incorporated herein by reference in its entirety; as well as, e.g., polyamino propoane sulfonic acid (AMPS), zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof.

Fluoride Ion Source

A composition of the present invention may comprise one or more fluoride ions. Fluoride ion sources are well know for use in oral care compositions as anticaries agents. Fluoride ions are contained in a number of oral care compositions for this purpose, particularly toothpastes. Patents disclosing such toothpastes include U.S. Pat. No. 3,538,230, Nov. 3, 1970 to Pader et al; U.S. Pat. No. 3,689,637, Sep. 5, 1972 to Pader; U.S. Pat. No. 3,711,604, Jan. 16, 1973 to Colodney et al; U.S. Pat. No. 3,911,104, Oct. 7, 1975 to Harrison; U.S. Pat. No. 3,935,306, Jan. 27, 1976 to Roberts et al; and U.S. Pat. No. 4,040,858, Aug. 9, 1977 to Wason.

Application of fluoride ions to dental enamel serves to protect teeth against decay. A wide variety of fluoride ion-yielding materials can be employed as sources of soluble fluoride in the instant compositions. Examples of suitable fluoride ion-yielding materials are found in Briner et al; U.S. Pat. No. 3,535,421; issued Oct. 20, 1970 and Widder et al; U.S. Pat. No. 3,678,154; issued Jul. 18, 1972, both patents being incorporated herein by reference. Preferred fluoride ion sources for use herein include sodium fluoride, potassium fluoride and ammonium fluoride. Sodium fluoride is particularly preferred. Preferably the instant compositions provide from about 50 ppm to 10,000 ppm, more preferably from about 100 to 3000 ppm, of fluoride ions in the aqueous solutions that contact dental surfaces when used with the strip 1.

Antimicrobial Agents

A composition of the present invention may comprise one or more antimicrobial agents. Such agents may include, but are not limited to, 5-chloro-2-(2,4-dichlorophenoxy)-phenol, commonly referred to as triclosan, and described in The Merck Index, 11th ed. (1989), pp. 1529 (entry no. 9573) in U.S. Pat. No. 3,506,720, and in European Patent Application No. 0,251,591 of Beecham Group, PLC, published Jan. 7, 1988; phthalic acid and its salts including, but not limited to those disclosed in U.S. Pat. No. 4,994,262, Feb. 19, 1991, substituted monoperthalic acid and its salts and esters as disclosed in U.S. Pat. No. 4,990,329, Feb. 5, 1991, U.S. Pat. No. 5,110,583, May 5, 1992 and U.S. Pat. No. 4,716,035, Dec. 29, 1987, all to Sampathkumar; preferably magnesium monoperoxy phthalate, chlorhexidine (Merck Index, no. 2090), alexidine (Merck Index, no. 222); hexetidine (Merck Index, no. 4624); sanguinarine (Merck Index, no. 8320); benzalkonium chloride (Merck Index, no. 1066); salicylanilide (Merck Index, no. 8299); domiphen bromide (Merck Index, no. 3411); cetylpyridinium chloride (CPC) (Merck Index, no. 2024; tetradecylpyridinium chloride (TPC); N-tetradecyl-4-ethylpyridinium chloride (TDEPC); octenidine; delmopinol, octapinol, and other piperidino derivatives; nicin preparations; zinc/stannous ion agents; antibiotics such as augmentin, amoxicillin, tetracycline, doxycycline, minocycline, and metronidazole; and analogs and salts of the above; essential oils including thymol, geraniol, carvacrol, citral, hinokitiol, eucalyptol, catechol (particularly 4-allyl catechol) and mixtures thereof; methyl salicylate; hydrogen peroxide; metal salts of chlorite and mixtures of all of the above.

Anti-Inflammatory Agents

A composition of the present invention may comprise one or more anti-inflammatory agents. Such agents may include, but are not limited to, non-steroidal anti-inflammatory agents or NSAIDs such as ketorolac, flurbiprofen, ibuprofen, naproxen, indomethacin, aspirin, ketoprofen, piroxicam and meclofenamic acid. Use of NSAIDs such as Ketorolac are claimed in U.S. Pat. No. 5,626,838, issued May 6, 1997, herein incorporated by reference. Disclosed therein are methods of preventing and, or treating primary and reoccurring squamous cell carcinoma of the oral cavity or oropharynx by topical administration to the oral cavity or oropharynx an effective amount of an NSAID.

Nutrients

A composition of the present invention may comprise one or more nutrients. Nutrients may improve the condition of the oral cavity and can be included in the oral care compositions of the present invention. Nutrients include minerals, vitamins, oral nutritional supplements, enteral nutritional supplements, and mixtures thereof.

Minerals include calcium, phosphorus, fluoride, zinc, manganese, potassium and mixtures thereof. These minerals are disclosed in Drug Facts and Comparisons (loose leaf drug information service), Wolters Kluer Company, St. Louis, Mo., 1997, pp 10-17; incorporated herein by reference.

Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Such vitamins are disclosed in Drug Facts and Comparisons (loose leaf drug information service), Wolters Kluer Company, St. Louis, Mo., 1997, pp. 3-10; incorporated herein by reference.

Oral nutritional supplements include amino acids, lipotropics, fish oil, and mixtures thereof, as disclosed in Drug Facts and Comparisons (loose leaf drug information service), Wolters Kluwer Company, St. Louis, Mo., 1997, pp. 54-54e; incorporated herein by reference. Amino acids include, but, are not limited to L-Tryptophan, L-Lysine, Methionine, Threonine, Levocarnitine or L-carnitine and mixtures thereof. Lipotropics include, but, are not limited to choline, inositol, betaine, linoleic acid, linolenic acid, and mixtures thereof. Fish oil contains large amounts of Omega-3 (N-3) Polyunsaturated fatty acids, eicosapentaenoic acid and docosahexaenoic acid.

Entenal nutritional supplements include, but, are not limited to protein products, glucose polymers, corn oil, safflower oil, medium chain triglycerides as disclosed in Drug Facts and Comparisons (loose leaf drug information service), Wolters Kluwer Company, St. Louis, Mo., 1997, pp. 55-57; incorporated herein by reference.

Enzymes

A composition of the present invention may comprise one or more compatible enzymes. Enzymes are biological catalysts of chemical reactions in living systems. Enzymes combine with the substrates on which they act forming an intermediate enzyme-substrate complex. This complex is then converted to a reaction product and a liberated enzyme which continues its specific enzymatic function.

Enzymes provide several benefits when used for cleansing of the oral cavity. Proteases break down salivary proteins which are absorbed onto the tooth surface and form the pellicle; the first layer of resulting plaque. Proteases along with lipases destroy bacteria by lysing proteins and lipids which form the structural component of bacterial cell walls and membranes. Dextranases break down the organic skeletal structure produced by bacteria that forms a matrix for bacterial adhesion. Proteases and amylases, not only prevent plaque formation, but also prevent the development of calculus by breaking-up the carbohydrate-protein complex that binds calcium, preventing mineralisation.

Enzymes useful in the present invention include any of the commercially available proteases, glucanohydrolases, endoglycosidases, amylases, mutanases, lipases and mucinases or compatible mixtures thereof. Preferred are the proteases, dextranases, endoglycosidases and mutanases, most preferred being papain, endoglycosidase or a mixture of dextranase and mutanase. Additional enzymes suitable for use in the present invention are disclosed in U.S. Pat. No. 5,000,939 to Dring et al., Mar. 19, 1991; U.S. Pat. No. 4,992,420 to Neeser, Feb. 12, 1991; U.S. Pat. No. 4,355,022 to Rabussay, Oct. 19, 1982; U.S. Pat. No. 4,154,815 to Pader, May 15, 1979; U.S. Pat. No. 4,058,595 to Colodney, Nov. 15, 1977; U.S. Pat. No. 3,991,177 to Virda et al., Nov. 9, 1976 and U.S. Pat. No. 3,696,191 to Weeks, Oct. 3, 1972; all incorporated herein by reference.

Mouth and Throat Products

A composition of the present invention may comprise one or more other materials commonly known mouth and throat products. Such products are disclosed in Drug Facts and Comparisons (loose leaf drug information service), Wolters Kluer Company, St. Louis, Mo., 1997, pp. 520b-527; incorporated herein by reference. These products include, but, are not limited to anti-fungal, antibiotic, anti-bad-breath and analgesic agents.

Antioxidants

A composition of the present invention may comprise one or more antioxidants. Antioxidants are generally recognized as useful in compositions such as those of the present invention. Antioxidants are disclosed in texts such as Cadenas and Packer, The Handbook of Antioxidants(c), 1996 by Marcel Dekker, Inc., incorporated herein by reference. Antioxidants that may be included in the oral care composition or substance of the present invention include, but are not limited to Vitamin E, ascorbic acid, Uric acid, carotenoids, Vitamin A, flavonoids and polyphenols, herbal antioxidants, melatonin, aminoindoles, lipoic acids and mixtures thereof.

Derivatives

Stereoisomer, tautomers, racemates, prodrugs, metabolites, pharmaceutically acceptable salts, bases, esters, structurally related compounds or solvates of the whitening agents, phosphates, fluoride ions, antimicrobial agents, anti-inflammatory agents, nutrients, enzymes, mouth/throat products and antioxidants are within the scope of the invention.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such a sarginine, lysine, and so forth.

Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl-bromides and others. Other pharmaceutically acceptable salts include the sulfate salt ethanolate and sulfate salts.

The term "stereoisomer", as used herein, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound herein encompasses the mixture of all possible stereochemically isomeric forms, which said compound may possess. Said mixture may contain all diastereomers and/or enantiomers of the basic molecular structure of said compound. All stereochemically isomeric forms of the compounds of the invention either in pure form or in admixture with each other are intended to fall within the scope of the present invention.

The compounds according to the invention may also exist in their tautomeric forms. Such forms, although not explicitly indicated in the compounds described herein, are intended to be included within the scope of the present invention.

For therapeutic use, the salts of the compounds according to the invention are those wherein the counter-ion is pharmaceutically or physiologically acceptable.

As used herein and unless otherwise stated, the term "solvate" includes any combination which may be formed by an agent of this invention with a suitable inorganic solvent (e.g. hydrates) or organic solvent, such as but not limited to alcohols, ketones, esters and the like.

The term "pro-drug" as used herein means the pharmacologically acceptable derivatives such as esters, amides and phosphates, such that the resulting in vivo biotransformation product of the derivative is the active drug. The reference by Goodman and Gilman (The Pharmacological Basis of Therapeutics, 8th Ed, McGraw-Hill, Int. Ed. 1992, "Biotransformation of Drugs", p 13-15) describing pro-drugs generally is hereby incorporated. Pro-drugs of the compounds of the invention can be prepared by modifying functional groups present in said component in such a way that the modifications are cleaved, either in routine manipulation or in vivo, to the parent component. Typical examples of pro-drugs are described for instance in WO 99/33795, WO 99/33815, WO 99/33793 and WO 99/33792 all incorporated herein by reference. Pro-drugs are characterized by increased bio-availability and are readily metabolized into the active inhibitors in vivo. Specific examples of prodrugs comprising cholesterol or vitamin A are described below.

Gelling Agents/Adhesive Agents

A composition of the present invention may comprise one or more gelling agents, particularly aqueous gelling agents. The gel is a high viscosity matrix formed from gelling agents known in the art. These gelling agents are safe for oral use, do not readily dissolve in saliva, and do not react with or inactivate the oral care compounds incorporated into them. Generally, the gelling agent is a swellable polymer. Furthermore, the gel formed with these agents can provide an optional adhesive attachment of the strip to the targeted area of the mouth.

The level of gelling agent to form the gel composition in order to thicken the liquid composition is from about 0.01 to 3%, 0.01 to 2%, 0.01 to 0.01 to 1% and preferably 0.01 to 2%. The level of gelling agent to form the gel composition having surface level adhesive properties is 2 to about 17%, from about 2% to about 15%, and preferably from about 2% to about 10%.

Suitable gelling agents useful in the present invention include carboxypolymethylene, carboxymethyl cellulose, carboxypropyl cellulose, polyoxamers, carrageenan, Veegum, carboxyvinyl polymers, and natural gums such as gum karaya, xanthan gum, Guar gum, gum arabic, gum tragacanth, alginates, locust bean gum and mixtures thereof. The preferable gelling agent for use in the present invention is carboxypolymethylene, obtained from B. F. Goodrich Company under the tradename Carbopol(R). Particularly preferable Carbopols include Carbopol 934, 940, 941, 956, 974 and mixtures thereof. Particularly preferred is Carbopol 974. Carboxypolymethylene is a slightly acidic vinyl polymer with active carboxyl groups. The normal concentration of various carboxypolymethylene resins in water, according to the manufacturer, is below about 2%. However, it has been found that by preparing supersaturated carboxypolymethylene compositions having an absolute concentration in the ranges specified above, suitable high viscosity oral gel compositions may be prepared.

The concentrated carboxypolymethylene gels have a number of important characteristics in addition to high viscosity. Enough carboxypolymethylene is added to the oral gel compositions beyond that required to provide high viscosity such that a significant quantity of saliva or water is required to lower the viscosity to the point that the composition may be diluted and washed out by saliva. The concentrated carboxypolymethylene composition also has a unique tackiness or stickiness which retains and seals the strip 1 against the targeted oral cavity surface it is affixed to, particularly teeth. However, care should be taken to avoid too much carboxypolymethylene thereby making insertion or withdrawal of the strip difficult.

If the oral care substance is an aqueous gel, the water present in the gel compositions should preferably be deionized and free of organic impurities. Water comprises from about 0.1% to 95%, preferably from about 5% to about 90%, and most preferably from about 10% to about 80%, by weight of the oral care substance. This amount of water includes the free water that is added plus that amount that is introduced with other materials.

A pH adjusting agent may also be added to optimize the storage stability of the gel and to make the substance safe for oral tissue. These pH adjusting agents, or buffers, can be any material which is suitable to adjust the pH of the oral care substance. Suitable materials include sodium bicarbonate, sodium phosphate, sodium hydroxide, ammonium hydroxide, sodium stannate, triethanolamine, citric acid, hydrochloric acid, sodium citrate, and combinations thereof. The pH adjusting agents are added in sufficient amounts so as to adjust the pH of the gel composition to about 4.5 to about 11, preferably from about 5.5 to about 8.5, and more preferably from about 6 to about 7. pH adjusting agents are generally present in an amount of from about 0.01% to about 15% and preferably from about 0.05% to about 5%, by weight of the oral care substance.

While the gel described above may provide an additional adhesiveness, other gelling agents may also be included in the formula to help the active ingredients adhere to the tissues of the oral cavity. Suitable agents include both polymers with limited water solubility as well as polymers lacking water solubility. These polymers deposit a thin film on both the oral cavity's soft and hard tissues when saliva combines with the instant composition. Suitable limited water solubility adhesives include: hydroxy ethyl or propyl cellulose. Adhesives lacking water solubility include: ethyl cellulose and polyox resins. Another possible adhesive suitable for use in the instant composition is polyvinylpyrrolidone with a molecular weight of about 50,000 to about 300,000. Still another possible adhesive suitable for use in the instant composition is a combination of Gantrez and the semisynthetic, water-soluble polymer carboxymethyl cellulose.

An additional carrier material may also be added to the oral care composition. Carrier materials can be humectants. Suitable humectants include glycerin, sorbitol, polyethylene glycol, propylene glycol, and other edible polyhydric alcohols. Humectants are generally present in an amount of from about 10% to about 95% and preferably from about 50% to about 80%, by weight of the oral care substance or composition. In addition to the above materials of the gel of the present invention, a number of other components can also be added to the oral care substance. Additional components include, but are not limited to, flavoring agents, sweetening agents, xylitol, opacifiers, coloring agents, and chelants such as ethylenediaminetetraacetic acid. These additional ingredients can also be used in place of the compounds disclosed above.

The oral care composition may be applied to the strip 1 using any known method. As already mentioned above, the composition may be present in cavities, within the body of, and/or on one or both faces the strip. Techniques for applying composition to a strip 1 are known to the skilled person such as coating, dipping, spraying. For application on one or both faces, preferred methods include spray application and dot or stripe application of the composition to the surface of the strip 1.

The strip according to the present invention achieves good penetration between the teeth, without causing patient discomfort by applying undue pressure. Further, said strip also overcomes the problem of additional salivation owning to the presence of the strip in the mouth which causes harmful active agents such as bleaching agents to leech into the oral cavity. Furthermore, said strip renders the teeth less sensitive to the external medium such as when eating or drinking and additionally provides the better adsorption of a component of an oral care composition. Additionally, the strip according to the present invention also can be used in teeth whitening processes during which it indicates the progress of the whitening process.

Combination with a Dental Device

One aspect of the present invention is a strip 1 as described herein for use with a dental device which is dental trough or brace. The dental device may function to apply pressure to the strip so providing a closer contact between the strip and enamel of the front teeth. The device may comprise functionality i.e. means for providing light (e.g. visible, UV and IR), heat, mechanical stimulation and electrical stimulation. The functionality may be provided by way of electrical components incorporated in the device, said functionality interacting with the composition of the strip 1. The electrical components can enhance treatments such as teeth whitening, pain relief, treating infections etc. Furthermore, the device may be autonomous (i.e. self contained) so that the subject is not restricted to procedures such as teeth whitening which normally require their presence on a dentist's chair and the equipment associate therewith. This further frees the dental chair for other patients. The use of a subject's own dental arch as a support for said functionality alleviates a dental practitioner from holding and directing an external source of illumination, heat, UV light, IR light etc., so enabling a practitioner to use both hands for performing dental manipulations.

Trough

Figure 3:
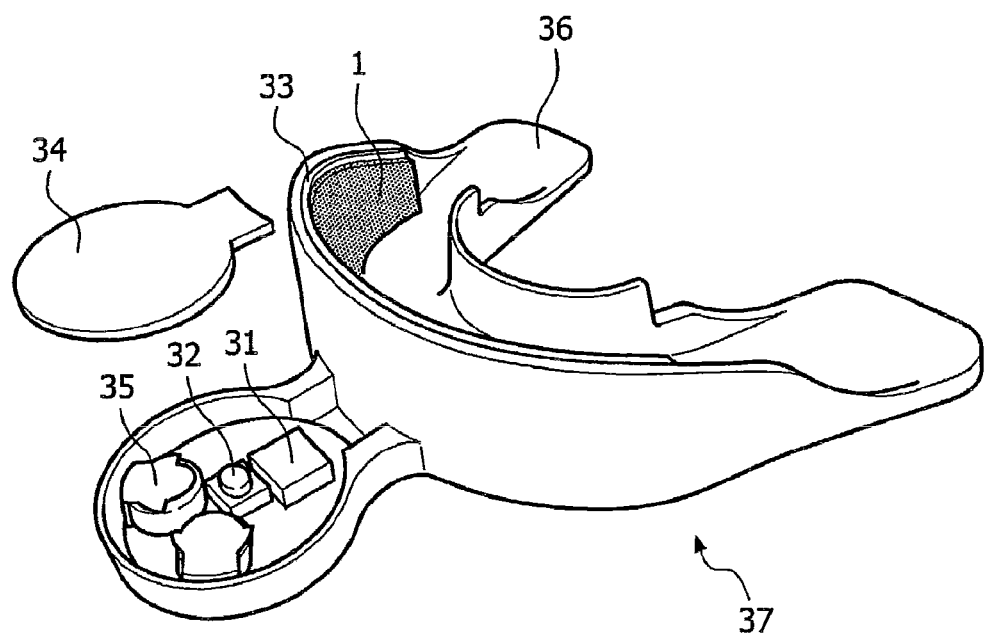
FIG. 3. A view of a dental though disposed with a strip according to the present invention.

FIG. 3 depicts an example of a dental device 37 provided with light functionality. It comprises a trough 36, disposed with a light-providing means which is an electroluminescent panel (EP) 33. A trough 36 according to the present invention can be any container shaped for the immersion of teeth and/or gums of the dental arch. The dental device is disposed with the EP 33 inside the trough 36, said EP interacting with active agents of the strip 1. The EP is connected to an inverter/controller 31 which drives the EP and is also capable of controlling timed treatment periods. The device is controllable by way of a switch 32, and is powered by two button batteries 35. Access to the batteries 35 and switch 32 is provided by means of a removable cover 34.

The trough is of a size, shape and flexibility to allow an adaptable fit on a wide variety of dental arches. Examples of suitable shapes include U-shaped, horse-shoe shaped troughs. A single size has the benefit of reduced mass-production costs, reduced storage space requirements and simpler consumer choice. In another embodiment of the present invention the trough is available in a variety of sizes and/or shapes. A choice of sizes and shapes provides a close-fitting appliance, and allows the appropriate degree of treatment to be delivered for a given size of dental arch. In another embodiment of the present invention the trough is custom-made for a particular dental arch. A custom-fitting device has the best fit which allows the functionality to be precisely delivered, and hence the appropriate degree of treatment to the dental arch.

The trough may further comprise one or more electrical components, which are means of providing mechanical stimulation (e.g. ultrasonic transducer, ultrasonic motor, magnetic motor), electrical stimulation (e.g. electrodes), light (e.g. LED, electroluminescence) or providing heat (e.g. LED, heating element). The trough further comprises a receiving or supporting means to hold one or more strips 1. An example of receiving means include the base of the trough, one or more grooves, one or more holes, one or more gripping means, one or more lugs, one more ridges, one or more slots etc.

Such a receiving means in the dental device allows agents which are activated or enhanced by, for example, light, heat, electrical and/or mechanical stimulation to be provided to a subject's teeth and/or gums, while being closely and precisely coupled to the source of light, heat, electrical or mechanical stimulation.

Brace

Where a dental device is a brace, it comprises wire elements suitable for clipping said brace to the teeth. The wire elements may be held in a polymeric support which is shaped to fit behind the teeth. A brace according to the invention is of the removable construction, well known in the art in orthodontic treatments, and as a 'fake brace' for cosmetic effect.

Figure 4:
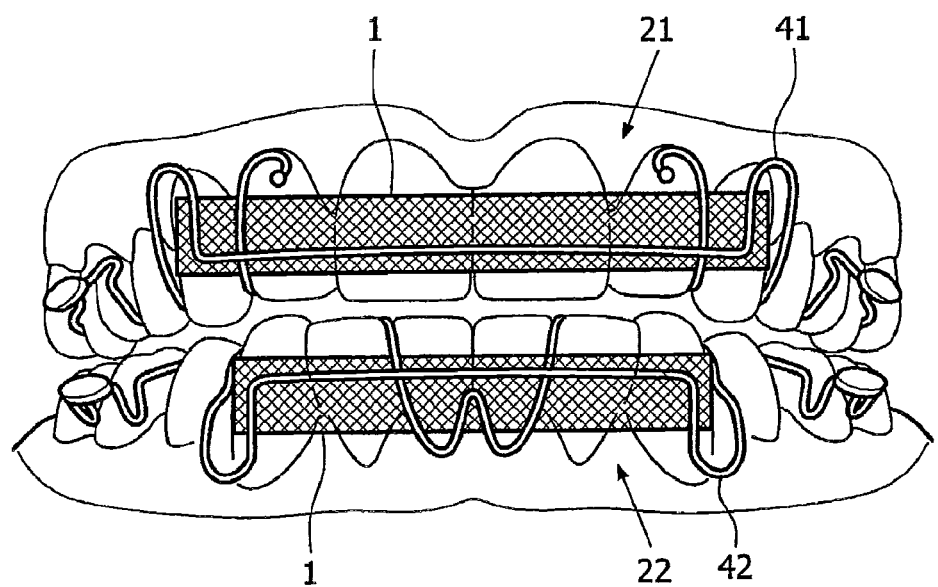
FIG. 4. A view of two strips attached to the upper and lower teeth respectively supported by an upper and lower brace.

Referring to FIG. 4, a brace 41 clips to the teeth of upper dental arch 21, and supports a strip 1 according to the present invention. Similarly, dental brace 42 fashioned to clip to the teeth of the lower dental arch 22, achieves the same effect of supporting a strip 1 according to the present invention.

Typically, a brace of the invention comprises one wire element which spans the front of the teeth. Optionally, other wire elements include one or more clips suitable for attachment to other teeth (e.g. rear molars, wisdom teeth etc). Material suitable for wire elements are known in the art of orthodontics and include, but are not limited to titanium, stainless steel, gold, silver, platinum, copper, ceramic, plastic, plastic/metal composite.

The polymeric support typically adopts the shape of the posterior (inner) face of the teeth. The support, as known in the art, is designed to lie behind the upper or lower teeth. It is usually in intimate contact with the posterior face of the upper or lower teeth, along at least part of the teeth. The polymeric support may be horse-shoe shaped. Where the brace is designed for the upper teeth, the support may adopt at least part of the shape of the upper palate. Material suitable for the support include, but are not limited to polycarbonate, polypropylene, rubberized polymer, composite, polymer.

The brace may be of a size, shape and flexibility to allow an adaptable fit on a wide variety of dental arches. Examples of suitable shapes include U-shaped, horse-shoe shaped. A single size has the benefit of reduced mass-production costs, reduced storage space requirements and simpler consumer choice. A choice of sizes and shapes provides a close-fitting appliance, and allows the appropriate degree of treatment to be delivered for a given size of dental arch.

Alternatively, the brace may be custom-made for a particular dental arch. A custom-fitting device has the best fit which allows the functionality to be precisely delivered, and hence the appropriate degree of treatment to the dental arch.

Methods of preparing a universal fitting brace, brace with a variety of sizes, and custom-fitting brace are known to the skilled person.

The brace may comprise one or more said electrical components, which are means of providing mechanical stimulation (e.g. ultrasonic transducer, ultrasonic motor, magnetic motor), electrical stimulation (e.g. electrodes), light (e.g. LED, electroluminescence) or providing heat (e.g. LED, heating element). The brace further comprises a receiving or supporting means to hold one or more strips 1. An example of receiving means one or more gripping means, one or more lugs, one more ridges, one or more slots etc.

Once applied to the teeth, the strip 1 lies between the teeth and the wire of the brace.

According to another aspect of the invention one or more wire elements may also provide aforementioned functionality. According to one aspect of the invention, one or more wires of the brace can provide heat (e.g. a wire element incorporating a heating element). According to one aspect of the invention, one or more wires of the brace provide light (e.g. a wire element incorporating an electroluminescent light). According to one aspect of the invention, one or more wires of the brace provide electrical stimulation (e.g. a wire element incorporating one or more electrodes).

Such brace form of the dental device allows agents which are activated or enhanced by, for example, light, heat, electrical, stimulation to be provided to a subject's teeth and/or gums, while being closely and precisely coupled to the source of light, heat, mechanical stimulation, electrical stimulation etc.

The material of the present invention creates an osmotic potential between the oral care composition and the teeth such that the composition moves naturally in the direction of the teeth. The osmotic effect is enhanced by heat and mechanical stimulation, thus leading to an improved activity when a strip 1 is combined with the dental device, particularly providing heat and mechanical stimulation.

Packaging

The strip 1 according to the present invention, may be packaged as a plurality of strips. Such a package may provide a course of treatment wherein the number of strips indicates the length of the treatment. For example, a teeth whitening course might be packaged to contain between 1 and 10 strips. Alternatively, a strip 1 might be singly packaged.

Types of packaging for the inserts of the invention are any suitable packaging systems and include, foil pouches, blister packs, foil-sealed trays, etc. Preferably the packaging is light impervious, so that active ingredients are not rendered inactive, for example, by sunlight exposure. Preferably, the packing is also moisture impervious so that composition present on the strip does not dry out. Preferably the packing provides a minimum of void volume. According to a preferred aspect of the invention, the packaging is a white blister pack. A blister pack conveys the advantage that the strip can be removed by applying pressure to the blister, so avoiding the need for excessive handling of the strip.

According to one embodiment of the invention, the white blister pack comprises a set of 10 or more recessed chambers on a polymeric sheet (e.g. polycarbonate, polystyrene, polyethylene), each chamber shaped to hold a strip. The blister pack further comprises a backing layer which attaches to the sheet and seals each strip in the chamber. The backing layer can be made from the same material as the sheet, or any other suitable material which breaks to allow the strip to be released from the blister upon the application of pressure. The chambers are optionally separated by perforations, allowing individual blisters pods to be detached from the sheet Kit Another embodiment of the present invention is a kit comprising one or more strips 1 as disclosed herein. A kit may optionally comprise a dental device.

According to one aspect of the invention, the kit provides one or more strips 1 which comprise a higher concentration of teeth whitening agent suitable for use by a dental practitioner, and one or more inserts which comprise a lower concentration of teeth whitening agent, suitable for home use. The dental device, where present may provide with one or more electrical components suitable for enhancing or stimulating the effect of said agents. The kit is intended for use in the first instance by a dental practitioner for whitening teeth: The strips comprising a higher concentration of agents are intended for use by the practitioner on the subject, and the strips comprising a lower concentration of agents are intended for use by non-practitioner, for example by the subject.

According to one aspect of the invention, the kit provides one or more strips 1 which comprise a high concentration of teeth whitening agent (e.g. 7, 8, 9, 10, 11, 12, 13, 14, 15, 16, 17, 18, 19, 20% peroxide or a value between the aforementioned concentrations) suitable for an intense treatment, and one or more inserts which comprise a lower concentration of teeth whitening agent (e.g. 0.01, 0.5, 1, 2, 3, 4, 5, 6, 7% peroxide or a value between the aforementioned concentrations). The strips comprising a higher concentration of agents remove most of the staining and are intended a short intense course e.g. one or two treatments, and the strips comprising a lower concentration of agents more gently remove the remaining stains and are intended for a slightly longer course e.g. 3 to 5 treatments.

According to one aspect of the invention, the kit provides one or more strips 1 which comprise regular concentration of teeth whitening agent suitable for a normal treatment (e.g. 5, 6, 7, 8% peroxide or a value between the aforementioned concentrations), and one or more inserts which comprise a low concentration of teeth whitening agent (e.g. 0.01, 0.5, 1, 2, 3, 4, 5, 6, 7% peroxide or a value between the aforementioned concentrations). The strips comprising a regular concentration of agents remove staining over a course of treatment e.g. 5 or 6 treatments, and the strips comprising a lower concentration of agents maintain the treatment.

According to another aspect of the invention, the kit provides one or more strips 1 which comprise a concentration of teeth whitening agent suitable for home teeth bleaching. The dental device of the kit, where present, is provided with one or more electrical components suitable for enhancing or stimulating the effect of the bleaching agents. The kit is intended for use by a non-practitioner for self-whitening of a subject's teeth.

Other versions of a kit according to the invention may comprise strips 1 incorporating one or more of the aforementioned agents e.g. one or more of whitening agents, phosphates, fluoride ions, antimicrobial agents, anti-inflammatory agents, nutrients, enzymes, mouth/throat products and antioxidants.

A kit may be provided with any combination of strips 1 as disclosed herein and a dental device provided with any combination of electrical components. The inserts may further comprise a combination of agents for example one or more of whitening agents, phosphates, fluoride ions, antimicrobial agents etc. Thus a kit may be suitable for providing a combination of therapies such as, for example, bleaching and bad breath, or pain relief and enhanced healing.

TABLE 1

Average data of VIVO foam MCF.03

| Test description | Test method | Unit | MCF.03 |
| --- | --- | --- | --- |
| Density | EN/ISO 845 Mod2 | $kg/m^3$ | 84 |
| Cell Structure (Visiocell) | C_PT_01.0 | µm | 170-220 |
| Wet-Out | C_PT_05.0 | sec. | 3 |
| Fluid capacity after draining | C_PT_05.2/ EN 13726-1 | g water/g product | 19 |
| Fluid capacity after compression | C_PT_05.3/ EN 13726-1 | g water/g product | 12 |
| MVTR | C_PT_13.0 | $g/m^2/day$ | 4072 |
| Lineair swell in length direction | C_PT_05.4 | % | 20 |
| Lineair swell in height direction | C_PT_05.5 | % | 18 |
| ER/RR-dry % elongation | ISO 1798 M1 | % | 220 |
| ER/RR-dry Strength at break | ISO 1798 M1 | kPa | 102 |
| Tear Resistance | ASTDM D3574 F M1 | N/cm | 2.8 |
| CDH 25% | ISO 3386_1 M1 | kPa | 3.6 |
| CDH 40% | ISO 3386_1 M1 | kPa | 4.9 |
| CDH 60% | ISO 3386_1 M1 | kPa | 9.5 |
| Compression set | ISO 1856/A M1 50% | % | 42.5 |
| Ball Rebound | ASTM/3574/H M1 | height loss % | 26 |
| Air Permeability | ISO 9237 M4 | $1/min/dm^2$ | 55 |

TABLE 2

Components of a teeth-whitening composition of the present invention.

| Component | Volume (ml) | m (g) | m (H$_2$O$_2$) | m/m % |
|---|---|---|---|---|
| glycerine | 500 | 630 | | 55.68 |
| water | 200 | 200 | | 17.52 |
| Peroxide solution 35% | 300 | 300 | 105 | 26.28 |
| EDTA | 1 | 1 | | 0.09 |
| BHT | 0.5 | 0.5 | | 0.04 |
| NaOH | to pH 6.5 | to pH 6.5 | | |
| TOTAL | 1000 | 1141.5 | 9.198 | 100 |

BHT is butylated hydroxytoluene, EDTA is ethylenediaminetetraacetic acid.

TABLE 3

Examples of foam loading quantities using a composition according to Table 2.

| g composition/g foam | g perox | m/m % H$_2$O$_2$/foam |
|---|---|---|
| 0.2 | 0.018396846 | 1.53 |
| 0.4 | 0.036793693 | 2.63 |
| 0.6 | 0.055190539 | 3.45 |
| 0.8 | 0.073587385 | 4.09 |
| 1 | 0.091984231 | 4.6 |
| 1.2 | 0.110381078 | 5.02 |
| 1.4 | 0.128777924 | 5.37 |
| 1.6 | 0.14717477 | 5.66 |
| 1.8 | 0.165571616 | 5.91 |
| 2 | 0.183968463 | 6.13 |
| 2.2 | 0.202365309 | 6.32 |
| 2.4 | 0.220762155 | 6.49 |
| 2.6 | 0.239159001 | 6.64 |
| 2.8 | 0.257555848 | 6.78 |
| 3 | 0.275952694 | 6.9 |

The invention claimed is:

1. A strip comprising polyurethane foam shaped for the application to the labile surface of the front teeth of a subject, which strip is provided with at least one oral care composition for delivery to a pre-determined area of the teeth of the subject, said at least one oral care composition comprising a pharmaceutically acceptable multi-carboxylate salty wherein upon application of the strip to the labile surface of the front teeth, the strip is only located on a front portion of the teeth.

2. The strip according to claim 1, wherein the pharmaceutically acceptable multi-carboxylate salt is an oxalate salt.

3. The strip according to claim 1, wherein the pharmaceutically acceptable multi-carboxylate salt is potassium oxalate.

4. The strip according to claim 1, wherein the pharmaceutically acceptable multi-carboxylate salt is a di- or a tri-carboxylate salt.

5. The strip according to claim 1, wherein the pharmaceutically acceptable multi-carboxylate salt is selected from the group consisting of adipate, aspartate, citrate, digluconate, fumarate, maleate, oxalate, pamoate, succinate, and tartrate.

6. The strip according to claim 1, wherein the salt is an alkali metal salt.

7. The strip according to claim 1, wherein the salt is a potassium salt.

8. The strip according to claim 1, wherein the pharmaceutically acceptable multi-carboxylic salt is present in the oral care composition in an amount in the range of 1 wt. % to 5 wt. % of the total weight of said at least one composition.

9. The strip according to claim 1, wherein said foam is treated at least on one side with silicones, fluorocarbons, wax.

10. The strip according to claim 1, wherein said foam has a fluid capacity after compression of between 10 and 14 g water/g.

11. The strip according to claim 1, wherein the foam has a density between 70 and 180 kg/m$^3$.

12. The strip according to claim 11, wherein said foam has a density between 90 and 150 kg/m3.

13. The strip according to claim 1, wherein said foam has a cell structure equal to or less than 220 micrometers.

14. The strip according to claim 1, wherein said at least one oral care composition further comprises at least one teeth whitening agent.

15. The strip according to claim 14, wherein said at least one teeth whitening agent is selected from the group consisting of metal ion free peroxides, organic peroxides, metal ion containing peroxides, metal chlorites, perborates, percarbonates, peroxyacids, monopersulfate, OXONE® (registered trademark of E.I. DuPont for monopersulfate oxidizing compound), ammonium persulfate, potassium persulfate, potassium monopersulfate, potassium peroxymonosulfate, potassium bisulfate, potassium sulfate and potassium peroxidisulfate, hydrogen peroxide, calcium peroxide, carbamide peroxide, urea peroxide, sodium percarbonate, sodium perborate, calcium hydroxide, calcium chlorite, barium chlorite, magnesium chlorite, lithium chlorite, potassium chlorate, hypochlorite, chlorine dioxide, magnesium carbonate and perhydrol urea and mixtures and derivatives thereof.

16. The strip according to claim 1, wherein said at least one oral care composition further comprises one or more fluoride ions selected from the group consisting of sodium fluoride, potassium fluoride and ammonium fluoride.

17. The strip according to claim 1, wherein said at least one oral care composition further comprises at least one antimicrobial agent.

18. The strip according to claim 17, wherein said at least one antimicrobial agent is selected from the group consisting of 5-chloro-2-(2,4-dichlorophenoxy)-phenol, phthalic acid and its salts, substituted monoperthalic acid and its salts and esters, magnesium monoperoxy phthalate, chlohexidine, alexidine, hexetidine, sanguinarine, bezalkonium chloride, salicylanilide, domiphen bromide, cetylpyridinium chloride (CPC), tertadecyl pridinium chloride (TPC), N-tetradecyl-4-ethylpyridinium chloride (TDEPC); octenidine; delmopinol, octapinol, nicin preparations, zinc/stannous ion agents, augmentin, amoxicillline, tetracycline, doxycycline, monocycline, metronidazole, thymol, geraniol, carvacrol, citral, hinokitiol, eucalyptol, catechol, 4-allyl catechol, methyl salicylate, hydrogen peroxide and metal salts of chlorite.

19. The strip according to claim 1, wherein said at least one oral care composition further comprises at least one or more anti-inflammatory agent.

20. The strip according to claim 19, wherein said at least one anti-inflammatory agent is selected from the groups consisting of ketorolac, flurbiprofen, ibuprofen, naproxen, indometacin, aspirin, ketoprofen, piroxicam and meclofenamic acid.

21. The strip according to claim 1, wherein said at least one oral care composition further comprises a nutrient selected from the group consisting of vitamins, oral nutritional supplements and enteral nutritional supplements.

22. The strip according to claim 1, wherein said at least one oral care composition further comprises at least one antioxidant.

23. The strip according to claim 22, wherein said at least one antioxidant is selected from the group consisting of Vitamin E, ascorbic acid, uric acid, carotenoids, Vitamin A, flavonoids and polyphenols, herbal antioxidants, melatonin, aminoindoles and lipoic acids.

24. The strip according to claim 1, wherein said at least one oral care composition further comprises 5 to 8% peroxide, 0-5% potassium nitrate, a fluoride capable of releasing fluoride ions in a concentration of 0-5000 ppm, and 30-70% glycerine.

25. The strip according to claim 1, wherein said at least one oral care composition further comprises at least one gelling agent.

26. The strip according to claim 25, wherein said at least one gelling agent is selected from the group consisting of carboxypoly-methylene, caroxymethyl cellulose, caroxyproyl cellulose, poloxamers, carrageenan, Veegum, caroxyvinyl polymers and natural gums.

27. The strip according to claim 1, wherein said at least one oral care composition is disposed on a reverse face.

28. A blister pack comprising one or more strips according to claim 1.

29. A kit comprising one or more strips according to claim 1 and a dental trough or brace.

30. A kit according to claim 29, wherein said dental brace or trough is provided with heat, light, electrical stimulation and/or mechanical stimulation means.

31. The strip according to claim 25, wherein said at least one gelling agent is selected from the group consisting of gum karaya, xanthan gum, Guar gum, gum Arabic, and gum tragacanth.

32. The strip according to claim 1, wherein the oral care composition is received throughout the polyurethane foam.

* * * * *

UNITED STATES PATENT AND TRADEMARK OFFICE
CERTIFICATE OF CORRECTION

PATENT NO. : 8,956,162 B2  
APPLICATION NO. : 13/528174  
DATED : February 17, 2015  
INVENTOR(S) : Guy De Vreese et al.

It is certified that error appears in the above-identified patent and that said Letters Patent is hereby corrected as shown below:

In the Claims

Column 25, Line 43, Claim 1, delete "salty" and insert -- salt, --

Column 26, Line 7, Claim 12, delete "kg/m3." and insert -- $kg/m^3$. --

Column 26, Line 41, Claim 18, delete "bezalkonium" and insert -- benzalkonium --

Column 26, Line 43, Claim 18, delete "pridinium" and insert -- pyridinium --

Column 26, Line 46, Claim 18, delete "amoxicillline," and insert -- amoxicillin, --

Column 26, Lines 46-47, Claim 18, delete "monocycline," and insert -- minocycline, --

Column 27, Line 13, Claim 26, delete "caroxymethyl" and insert -- carboxymethyl --

Column 27, Lines 13-14, Claim 26, delete "caroxyproyl" and insert -- carboxyproyl --

Column 27, Lines 14-15, Claim 26, delete "caroxyvinyl" and insert -- carboxyvinyl --

Signed and Sealed this  
Second Day of June, 2015

Michelle K. Lee  
*Director of the United States Patent and Trademark Office*